United States Patent [19]

Eigen et al.

[11] Patent Number: 4,737,359
[45] Date of Patent: Apr. 12, 1988

[54] CONTROL OF DENTAL PLAQUE AND CARIES USING EMULSAN

[75] Inventors: Edward Eigen, East Brunswick; Alexander J. Simone, Somerset, both of N.J.

[73] Assignee: Colgate-Palmolive Company, New York, N.Y.

[21] Appl. No.: 886,498

[22] Filed: Sep. 8, 1986

Related U.S. Application Data

[62] Division of Ser. No. 724,376, Apr. 18, 1985, Pat. No. 4,619,825.

[51] Int. Cl.[4] ................................. A61K 7/16
[52] U.S. Cl. ......................... 424/50; 424/49; 424/51; 424/52; 424/53; 424/54; 424/55; 424/56; 424/57; 424/58; 514/835
[58] Field of Search .................. 424/49–58; 514/835

[56] References Cited

U.S. PATENT DOCUMENTS

| | | | |
|---|---|---|---|
| 3,963,832 | 6/1976 | Hashimoto et al. | 424/49 |
| 4,276,094 | 6/1981 | Gutnick et al. | 435/822 |
| 4,483,848 | 11/1984 | Cox et al. | 424/49 |
| 4,619,825 | 10/1986 | Eigen et al. | 424/49 |

FOREIGN PATENT DOCUMENTS 0178443  4/1986  European Pat. Off. .

OTHER PUBLICATIONS

Rosenthal, in *Cosmetics: Science and Technology;* 2nd ed., vol. 1, Wiley–Interscience, N.Y., 1972, pp. 547–551.
ADA, *Accepted Dental Therapeutics,* 38th ed., American Dental Association, Chicago, Ill., 1979, p. 342.
Rosenberg et al., *Infection and Immunity,* 831, (1983).
Rosen et al., in *Molecular Basis of Oral Microbial Adhesion,* American Society for Microbiology, Wash., D.C., 1985, p. 73.
Keyes et al., *Journal of Oral Therapeutics and Pharmacology,* vol. 3, No. 3, 157–173, (1966), copyright © 1966 by The Williams & Wilkins Co.
Keyes, *Animal Models in Cariology,* Proceedings of a Symposium and Workshop on Animal Models in Cariology, Apr. 21–23, 1980, Sturbridge, Mass.
Gibbons et al., *Infection and Immunity,* vol. 41, No. 1, 1190–1196, (1983).
Rosen et al., in *Molecular Basis of Oral Microbial Adhesion,* edited by Mergenhagen and Rosen, pp. 69–77, American Society for Microbiology, Wash. D.C., 1985.

*Primary Examiner*—J. R. Brown
*Assistant Examiner*—F. T. Moezie
*Attorney, Agent, or Firm*—Robert L. Stone; Murray M. Grill; Herbert S. Sylvester

[57] ABSTRACT

Plaque is inhibited and oral hygiene promoted including reduction in caries formation by dispersing emulsan in water and contacting the aqueous dispersion with dental surfaces. Emulsan may be dispersed in dental preparation toothpaste or mouthwash.

13 Claims, No Drawings

CONTROL OF DENTAL PLAQUE AND CARIES USING EMULSAN

This is a division of application Ser. No. 724,376, filed Apr. 18, 1985, now U.S. Pat. No. 4,619,825, granted Oct. 28, 1986.

This invention relates to control of dental plaque and caries, thereby improving oral hygiene.

Plaque formation on teeth is unsightly and can lead to incidence of further oral hygiene conditions, such as dental caries, although direct correlation between amounts of plaque and amounts of such further conditions has not been established. Dental plaque is a deposit coating of a mucilaginous and gelatinoid-type material on teeth which is readily produced by and/or invaded by colonies of bacteria. If not controlled, the normal metabolic activity of these bacteria in the plaque can produce various acids such as acrtic, butyric and lactic acids, which may react with calcium of dental enamel resulting in decalcification and dental caries formation. Other microbial by-products may attack soft gum tissue leading to gingivitis. Thus, dental plaque is considered to be a primary cause of dental caries and gingivitis and reduction and control of dental plaque are essential to sound oral hygiene.

Dental caries is generally recognized to be caused by microorganisms such as *Streptococcus mutans*. Dietary sucrose is believed to be the principal material utilized by the *S. mutans* in plaque, resulting in acid production and subsequent decalcification. Glucans produced from sucrose by the *S. mutans* glucosyltransferases (GTF) have been indicated as a primary factor in adherence of the bacteria to smooth surfaces.

Lectins, or hemagglutinins, generally comprise a large number of crude or purified proteins or glycoproteins of plant or animal origin which have been characterized or identified by their ability to agglutinate suspensions of red blood cells derived from human blood or blood of other animals. Lectins bind specific carbohydrates and therefore contribute significantly to the ability of bacteria to attach to various surfaces. Bacterial surface letins bind carbohydrates on red blood cells, in salivary pellicle and on the surfaces of other cells. This specific binding interaction can be reversed or prevented by saturating the bacterial lectin sites with proper carbohydrate material. Galactose and galactosamine are sugars most commonly bound by surface lectins of oral microorganisms, notably *S. mutans*.

Attempts to reduce and control dental plaque have been made by inhibiting the ability of *S. mutans* to colonize. However, possibly due to the vitality of *S. mutans* when routinely contacted with food carbohydrates, it has been very difficult to effectively inhibit its growth and thereby promote oral hygiene, without undesirable antimicrobial-caused side effects. Improved means to reduce dental plaque and assist in promoting oral hygiene by reducing dental caries and gingivitis continues to be under urgent investigation. In the meantime, dental caries and gingivitis remain as great problems in the field of oral hygiene.

Recently, research has focussed on whether the cell-surface hydrophobicity exhibited when bacteria such as *S. mutans* adhere to oral tissues or dental plaque can be correlated to cell-surface hydrophobicity exhibited when such bacteria adhere to hydrocarbons. For instance, the article "Inhibition of Bacterial Adherence to Hydrocarbons and Epithelial Cells by Emulsan", *Infection and Immunity*, E. Rosenberg, Gottlieb and M. Rosenberg, Vol. 39, pages 1024–1028 (1983) compares the ability of emulsan to inhibit bacterial attachment to hydrocarbons and to buccal epithelial cells under in vitro conditions. It is reported in this study that the bacterial attachment to buccal epithelial cells is reversed by saliva. It is, therefore, doubtful to expect similar inhibition under in vivo conditions.

Various types of emulsans, their chemical and physical properties including emulsification with hydrocarbons are described in a series of patents, viz: U.S. Patents to D. L. Glutnick and co-inventors, U.S. Pat. Nos.: 4,230,801, 4,234,689, 4,276,094, 4,311,829, 4,311,830, 4,311,831, 4,311,832, 4,380,504, 4,395,353, and 4,359,354.

The disclosures of these patents are incorporated herein by reference.

There has also been literature discussing the pronounced cell-surface hydrophobicity of unidentified microorganisms from scrapings from supragingival plaque as measured by adherence to several hydrocarbon substrates, particularly the article "Cell Surface Hydrophobicity of Dental Plaque Microorganisms In Situ", M. Rosenberg, Judes and Weiss, *Infection and Immunity*, Vol. 42, pages 831–834 (1983).

Nevertheless, based on what is known and further reasearch, such as is described in the article "Comparative Hydrophobicities of Oral Bacteria and Their Adherence to Salivary Pellicles", Gibbons and Etherden, *Infection and Immunity*, Vol. 41, pages 1190–1196, (1983), wherein it was shown that although some oral microorganisms are indeed strongly hydrophobic, those microorganisms implicated in caries formation and many responsible for gingivitis are only moderately hydrophobic. In fact, the authors concluded: "Although there was a general correlation between the hydrophobicity of the bacterial strains studied and their adherence to experimental pellicles, it seems unlikely that hydrophobic interactions per se can account for the highly specific way in which bacteria attach to teeth and other oral tissues."

Thus, considering the prior art in which particular materials such as emulsans which have in vitro effectiveness in inhibiting bacterial adherence to buccal epithelial cells as well as to hydrocarbons due to interference with cell-surface hydrophobic interactions, the ordinarily skilled researcher would not expect, therefore, that emulsans would produce a high level of effectiveness in reducing plaque formation and promoting oral hygiene in other ways, such as in reducing caries formation, particularly since microorganisms such as *S. mutans* are only moderately hydrophobic. Indeed at an address titled "Bacterial Surfaces, Salivary Pellicles and Plaque Formation," at the International Workshop of Molecular Interactions in Oral Microbial Adherence and Aggregation, June 4–8, 1984, Philadelphia, Pa., Dr. B. Rosan asserted that hydrophobicity plays a very minor role in attachment of oral bacteria to surfaces and further that there are serious shortcomings in the validity of hydrocarbon hydrophobicity testing for correlation with oral conditions.

(Rosan, B., R. Eifert and E. Golub, 1985. Bacterial surfaces, salivary pellicles and plaque formation. Pages 69–76 in S. E. Mergenhagen and B. Rosan (ed.). Molecular Basis of Oral Microbial Adhesion, American Society for Microbiology, Wash., D.C.)

It is an advantage of the present invention that plaque formation is inhibited and oral hygiene is promoted.

It is a further advantage of this invention that plaque is removed from dental enamel, thereby promoting oral hygiene.

It is a further advantage of this invention that caries development is retarded. Further advantages will be apparent from consideration of the following specification.

In accordance with certain of its aspects, this invention relates to a method for inhibiting dental plaque and promoting oral hygiene comprising dispersing an effective plaque-inhibiting amount of emulsan in water and contacting the aqueous dispersion of emulsan with natural or artificial dental surfaces.

As mentioned, in spite of its cell-surface hydrophobicity characteristics, it was quite unexpected that emulsan could be effective in promoting oral hygiene, particularly in conjunction with an oral environment (that is, in vivo), by reducing plaque formation through inhibition of attachment of *S. mutans*, for instance, in view of the report in *Infection and Immunity*, Vol. 39, cited above, that saliva reverses inhibition by emulsan of bacterial attachment to buccal epithelial cells. Without being bound to a theory for its effectiveness, the presence of a galactosamine backbone in emulsan permits emulsan to inhibit attachment of *S. mutans* due to the presence of a galactose or galactosamine-specific lectin on the surface of *S. mutans*. Alternatively, emulsan may desorb *S. mutans* that have previously attached to dental surfaces. Further, the hydrophobicity of emulsan permits emulsan to be effective without saliva being able to effect a reversal of inhibition of bacterial attachment. Moreover, lipophilic groups in emulsan disrupt hydrophobic bonds. There are attached to the galactosamine backbone of emulsan fatty acid derivatives having $C_2$–$C_{22}$ chain lengths, with an average of $C_{12}$. In other words, emulsan provides a polymeric form of an analog of galactose which is specific for bacterial lectins and contains groups which disrupt hydrophobic bonds. The rapidity with which emulsan acts upon *S. mutans* is indicative that both cell-surface hydrophobicity and galactosamine effects occur together.

Emulsan is produced by Acinetobacter Sp. ATCC 31012. It is a polyanionic biopolymer described in several variants of extracellular microbial lipopolysaccharides and their derivatives selected from the group consisting of:

(a) the extracellular microbial protein-associated lipopolysaccharides (herein collectively called "α-emulsans") produced by Acinetobacter Sp. ATCC 31012 and its mutants, in which the lipopolysaccharide components (herein collectively called "apo-α-emulsans") are completely N-acylated and partially O-acylated heteropolysaccharides made up of major amounts of D-galactosamine and an aminouronic acid, such apo-α-emulsans containing at least 5% by weight of fatty acid esters in which (1) the fatty acids contain from about 10 to about 18 carbon atoms; and (2) about 50% by weight or more of such fatty acids are composed of 2-hydroxydodecanoic acid and 3-hydroxydodecanoic acid;

(b) the deproteinized extracellular microbial lipopolysaccharides (herein collectively cassed "apo-α-emulsans") obtained from the α-emulsans produced by Acinetobacter Sp. ATCC 31012 and its mutants, the apo-α-emulsans being completely N-acylated and partially O-acylated heteropolysaccharides made up of major amounts of D-galactosamine and an aminouronic acid, the apo-α-emulsans containing at least 5% by weight of fatty acid esters in which (1) the fatty acids contain from about 10 to about 18 carbon atoms; and (2) about 50% by weight or more of such fatty acids are composed of 2-hydroxydodecanoic acid and 3-hydroxydodecanoic acid;

(c) the deproteinized extracellular microbial polysaccharides (herein collectively called "apo-β-emulsans") obtained from the β-emulsans produced by Acinetobacter Sp. ATCC 31012 and its mutants, the apo-β-emulsans being completely N-acylated and partially O-acylated heteropolysaccharides made up of major amounts of D-galactosamine and an aminouronic acid, the apo-β-emulsans containing not more than 5% by weight of fatty acid esters in which (i) the fatty acids contain from about 10 to about 18 carbon atoms; and (2) less than 50% by weight of such fatty acids are composed of 2-hydroxydodecanoic acid and 3-hydroxydodecanoic acid;

(d) the O-deacylated extracellular protein-associated microbial polysaccharides (herein collectively called the "ψ-emulsans") obtained from the emulsans produced by Acinetobacter Sp. ATCC 31012 and its mutants, the protein-free components of such ψ-emulsans being completely N-acylated heteropolysaccharides made up of major amounts of D-galactosamine and an aminouronic acid and containing from 0 to 1% by weight of fatty acid esters in which, when present, the fatty acids contain from about 10 to about 18 carbon atoms;

(e) the deproteinized O-deacylated extracellular microbial polysaccharides (herein colectively called the "apo-ψ-emulsans") derived from either α-emulsans, β-emulsans, ψ-emulsans, apo-α-emulsans or apo-β-emulsans, the apo-ψ-emulsans being completely N-acylated heteropolysaccharides made up of major amounts of D-galactosamine and an aminouronic acid and containing from 0 to 1% by weight of fatty acid esters in which, when present, the fatty acids contain from about 10 to about 18 carbon atoms;

(f) the deproteinized O-deacylated extracellular microbial polysaccharides (herein collectively called the "proemulsans") derived from either α-emulsans, β-emulsans, ψ-emulsans, apo-α-emulsans, apo-β-emulsans or apo-ψ-emulsans, the proemulsans being poly (D-galactosamine/amino uronic acid) biopolymers in which (1) none of the hydroxy group are acylated; and (2) from none to all of the amino groups are acylated; and (g) the divalent metal, ammonium and quaternary ammonium salts of such α-emulsans, apo-α-emulsans, apo-β-emulsans, β-emulsans, apo-ψ-emulsans and proemulsans.

A lexicon of words has been developed to identify and refer to the various types of extracellular microbial polysaccharides and their semi-synthetic derivatives which are derived from Acinetobacter Sp. ATCC 31012 and its mutants. These words are "emulsans", "α-emulsans", "β-emulsans", "ψ-emulsans", "apoemulsans", "apo-α-emulsans", "apo-β-emulsans", "apo-ψ-emulsans" and "proemulsans", which are defined as follows:

The name "emulsan", which reflects the polysaccharide structure of these compounds and the exceptional emulsion stabilizing activity of the biologically produced materials, was created to identify generically those extracellular microbial protein-associated lipoheteropolysaccharides produced by Acinetobacter Sp. ATCC 31012 and its mutants, which may be subdivided into the α-emulsans and the β-emulsans. The name "apo-emulsan", the prefix of which is derived from the Greek word "απο" meaning "from", has been created to identify generically those deproteinized lipopolysaccharides obtained from the emulsans.

The name "α-emulsan" defines those extracellular microbial protein-associated lipopolysaccharides produced by Acinetobacter Sp. ATCC 31012 and its mutants in which the lipopolysaccharide components (i.e., without the associated protein) are completely N-acylated and partially O-acylated heteropolysaccharids made up of major amounts of D-glactosamine and an aminouronic acid, the lipopolysaccharide components containing at least 5% by weight of fatty acid esters in which (1) the fatty acids contain from about 10 to about 18 carbons atoms; and (2) about 50% by weight or more of such fatty acids are composed of 2-hydroxydodecanoic acid and 3-hydroxydodecanoic acid. It follows, therefore, that the deproteinized α-emulsan is named "apo-α-emulsan".

The name "β-emulsan" defines those extracellular microbial protein-associated lipopolysaccharides produced by Acinetobacter Sp. ATCC 31012 and its mutants in which the lipopolysaccharide components (i.e., without the associated protein) are completely N-acylated and partially O-acylated heteropolysaccharides made up of major amounts of D-galactosamine and an aminouronic acid, the lipopolysaccharide components containing less than 5% by weight of fatty acid esters in which (1) the fatty acids contain from about 10 to about 18 carbon atoms; and (2) less than 50% by weight of such fatty acids are composed of 2-hydroxydodecanoic acid. The deproteinized β-emulsan is named "apo-β-emulsan".

The name "ψ-emulsan" defines the O-deacylated extracellular protein-associated microbial polysaccharides obtained from the emulsans, the protein-free components of such ψ-emulsans being completely N-acylated heteropolysaccharides made up of major amounts of D-galactosamine and an aminouronic acid and containing from 0 to 1% of fatty acid esters in which, when present, the fatty acids contain from about 10 to about 18 carbon atoms. These protein-free components are named "apo-ψ-emulsan", regardless of how they are prepared.

The name "proemulsan" defines the deproteinized O-deacylated extracellular microbial polysaccharide in which the poly(D-galactosamine/aminouronic acid) biopolymers are characterized by (1) none of the hydroxy groups being acylated; and (2) from none to all of the amino groups being acylated. The proemulsans have no emulsifying activity.

The bioemulsifiers which were inherently formed in experimental work concerning the growth of RAG-1 on crude oil or hexadecane were β-emulsans, in which the lipopolysaccharide contained from 2 to 3 percent by weight of fatty acid esters. The β-emulsans, therefore have been given the common name "protoemulsan", the prefix of which is derived from the Greek word "πρῶτος" meaning "first".

The α-emulsans have been given the common name "neoemulsan", the prefix having derived from the Greek word "νέος" meaning "new". Because the ψ-emulsans have only about one-half the emulsifying activity of the α-emulsans, the ψ-emulsans have been given the common name "pseudoemulsan".

As used herein, the term "Acinetobacter Sp. ATCC 31012 and its mutants" refers not only to the organism (i.e. strain RAG-1) and its spontaneous and chemically- and physically-induced mutants and recombinants which produce emulsans, but to all microorganisms (whatever the genus) derived by using recombinant DNA techniques to insert genetic information from strain RAG-1, and such mutants which are responsible for the production of the bioemulsifiers into the DNA-based genetic code of such "recombined" microorganisms such that they are capable of biosynthesizing α-emulsans or β-emulsans (or the apoemulsans), depending upon the primary assimilable carbon source used to grow the organism.

Emulsan in its various forms and its characteristics are described in the several U.S. patents to Gutnick and co-inventors set forth above and incorporated herein by reference. The several forms are suitable for use in the present invention to promote oral hygiene. Apo-α-emulsan is an example of a particularly effective emulsan.

In the practice of the present invention, a plaque-inhibiting amount of emulsan is dispersed in water. A minor amount of (less than half) undissolved emulsan may remain or the dispersed emulsans may be completely dissolved. Typical effective amounts may be as little as about 0.05% of dispersed emulsan in water and as much as about 10 or more, preferably about 0.1-3% and most preferably about 0.25-1%.

Under normal ambient mouth cleaning or mouth rinsing conditions, the emulsan solution is contacted with dental surfaces. This may be done directly in a mammalian oral cavity or mouth on natural or artificial dental surfaces, that is on teeth or dentures, in the presence of saliva or on artificial dental surfaces when removed from the oral cavity. This procedure results in substantial reduction in plaque-film already present on the dental surfaces as well as reducing the tendency of plaque to form or re-form on such surfaces, marked reduction in the presence of aerobe and facultative microorganisms such as S. mutans (a facultative microorganism) and accompanying significant promotion of oral hygiene such as by reduction in caries formation.

Saliva may not be required for emulsan to inhibit attachment of S. mutans to dental surfaces. Moreover, with respect to other microorganisms, such as S. sanguis, saliva would not effect a reversal of the ability of emulsan to inhibit attachment to saliva-coated oral surfaces. Rather, saliva would not interfere with detachment of S. sanguis from oral surfaces.

In accordance with an aspect of the invention, there is provided a dental preparation toothpaste or mouthwash comprising a plaque-inhibiting amount of emulsan and a dental vehicle containing water in sufficient amount to dissolve said plaque-inhibiting amount of emulsan, said vehicle further containing a humectant and gelling agent when said preparation is a toothpaste and a non-toxic alcohol when said preparation is a mouthwash.

In a toothpaste, the liquid and solid vehicle materials should necessarily be proportioned to form a creamy or gel mass of desired consistency which is extrudable from a collapsible lined or unlined aluminum tube, lined lead tube, laminate tube, mechanically operated dispenser or pressure operated dispenser. In general, the liquids in the dental cream will comprise chiefly water and humectant, such as glycerine, sorbitol, propylene glycol, polyethylene glycol, etc., including suitable humectant mixtures. It is advantageous usually to use a mixture of both water and a humectant such as glycerine or sorbitol. The total liquid content will generally be about 20-75% by weight of the formulation. It is preferred to use a gelling agent in the dental cream, the natural and synthetic gums and gum-like materials, e.g., Irish moss, gum tragacanth, sodium carboxymethyl cellulose, polyvinyl pyrrolidone, starch, and the like, usually, in an amount up to about 10% by weight, and preferably about 0.5-5% of the formulation. Emulsan can assist in thickening the composition.

In order to assist in cleaning of dental surfaces, toothpastes also typically contain a water-insoluble polishing agent. There is a relatively large number of such materials known in the art. Representative materials include, for example, insoluble sodium metaphosphate, dicalcium phosphate dihydrate, anhydrous dicalcium phosphate, calcium carbonate, hydrated alumina, silica, bentonite, etc., including suitable mixtures thereof. In general, these polishing agents will conmprise a major proportion by weight of the solid ingredients. The polishing agent content is variable, but will generally be about 20-75% by weight.

In a mouthwash, the non-toxic alcohol is typically present in amount of about 5-25% by weight.

The alcohol component of a mouthwash is a non-toxic alcohol such as isopropanol or ethanol, preferably utilizing denaturing components which also function as flavoring agents. These flavoring agents are used in an amount between about 1% and 2% of the total alcohol content of the mouthwash.

Various adjuvant materials can be incorporated in such dental preparations. Added materials in the formulation which do not substantially adversely effect the properties and characteristics can be suitably selected and used in proper amount depending upon the particular type of preparation. Such materials may be used as soluble saccharin, flavoring oils (e.g. oils of spearmint, peppermint, wintergreen), coloring or whitening agents (e.g., titanium dioxide), preservatives (e.g., sodium benzoate, etc.), menthol and the like. Various other materials can be added such as surface-active agents, e.g. sodium lauryl and $C_{10}-C_{18}$ fatty acid amides of amino carboxylic acid compounds, typically sodium lauroyl and palmitoly sarcosides. Nonionic surface active agents such as block copolymers of polyoxyethylene and polyoxypropylene can be employed, although emulsan can also suitably provide their effects and reduce need for their presence. Other suitable materials are chlorophyllin and various ammoniated ingredients, such as urea, diammonium phosphate and mixtures thereof.

The preparations suitably may also contain a fluorine-containing compound having a beneficial effect on the care and hygiene of the oral cavity, e.g., diminution of enamel solubility in acid and protection of the teeth against decay. Examples thereof include sodium fluoride, stannous fluoride, potassium fluoride, potassium stannous fluoride ($SnF_2KF$), sodium hexafluorostannate, stannous chlorofluoride, sodium fluorozirconate, and sodium monofluorophosphate. These materials, which dissociate or release fluorine-containing ions in water, suitably may be present in an effective but non-toxic amount, usually within the range of about 0.01 to 1% by weight of the water soluble fluorine content thereof.

The present invention is more fully described and illustrated in the following examples. It is to be understood, however, that the invention is not to be limited to any specific form of materials or conditions set forth in the examples, but is limited solely by the description in the specification and the appended claims. All parts are by weight unless otherwise specified.

EXAMPLE 1

In vitro tests

The ability of emulsan (apo-α-emulsan) to remove S. mutans from in vitro plaque is compared with the ability of galactose to do the same by Glass Slide Plaque Assay method.

The method is the modified method of Evans et al, Journal of Dental Research, Vol. 56 (6), pages 559-567, (1977), which capitalizes on the ability of many oral streptococci (including S. mutans) to adhere to glass as well as oral surfaces. In the modified method, the organisms are inoculated into broth tubes containing 5.0 ml of Todd-Hewitt Broth (BBL) supplemented with 5% sucrose (w/v). Each tube contains a uniformly cut and cleaned glass microscope slide. Tubes are incubated anaerobically at 37° C. for 40-48 hours and plaque forms on the slides as the bacteria grow and metabolize.

The slides are removed from the growth medium, rinsed for 20 seconds in an agitated buffer to remove loosely bound plaque and placed in tubes containing either control (phosphate buffered KCl, pH 6.8) or treatment (emulsan) solutions. Control and treatment tubes (with slides) are places on a rotary shaker at 200 rpm at room temperature for the time indicated. Slides are then removed from the tubes, rinsed and transferred to tubes containing 1.0N sodium hydroxide which strips remaining plaque from the slides. The optical densities of the resulting sodium hydroxide suspensions are individually measured at A540 using a Beckman Model 25 Spectophotometer. The treatment values obtained are compared to control values to approximate the amount of in vitro plaque removed by the treatment. At least 5 replicates per treatment per trial are performed to minimize variation among slides.

The results are:

TABLE 1

| Anti-plaque Additive | Concentration of Additive in Water | Time of Contact | Reduction of S. mutans plaque |
|---|---|---|---|
| Galactose | 5% | 2 hours | 31% |
| Galactose | 10% | 2 hours | 66% |
| Apo-α-emulsan | 0.1% | 30 minutes | 83% |

Emulsan is demonstrated even in low concentration in vitro to achieve greater effectiveness in removing S. mutans plaque much more quickly than does galactose.

In a further test using the Glass Slide Plaque Assay, 1% apo-α-emulsan reduces S. mutans 6715WT13 plaque by about 71% after 2 hours and also effects reductions of about 62% and 63% in plaque formed by S. salivarius SS2 and S. sanguis FC-1, respectively (although it does not measurably reduce S. sanguis 34 and S. mitis plaque in this assay).

EXAMPLE 2

In vivo tests

A streptomycin-resistant strain of S. mutans (6715-41) was used to infect the mouths of hamsters prior to the study. One of the groups, however, is inoculated with the S. mutans organisms pre-treated with apo-α-emulsan in order to determine whether the lectin-carbohydrate bonding mechanism, blocking the lectin sites on the organism, would prevent its adherence. Inoculations are once a day for three successive days. The groups in the study are:

Group Number

I. Inoculated with *S. mutans* 6715-41 and given 1% emulsan in the drinking water.
II Inoculated with emulsan pre-treated *S. mutans* 6715-41 and given water to drink.
III. Water control, inoculated with *S. mutans* 6715-41.

All groups are fed the Keyes 2000 caries-producing diet. After three weeks, five hamsters from each group are sacrificed, the lower jaws removed, placed in buffer, sonicated for 25 seconds to disperse plaque and plate counts made. *S. mutans* is counted in a selective agar medium further supplemented with Streptomycin to retard the growth of other bacteria. Total aerobes are also counted to give an indication as to effects on total plaque organisms. The evaluation is repeated after five weeks and nine weeks. In the five-week and nine-week evaluations, the lower jaws are scored for caries. The results are set forth in Tables 2, 3 and 4:

TABLE 2

| Group | % Reduction in *S. mutans* Compared with Control After | | |
|---|---|---|---|
|  | 3 weeks | 5 weeks | 9 weeks |
| I Emulsan Drinking | 51 | 77 | 41 |
| II Emulsan Pretreatment | 61 | 0 | 26 |

TABLE 3

| Group | % Reduction in Total Aerobes Compared with Control After | | |
|---|---|---|---|
|  | 3 weeks | 5 weeks | 9 weeks |
| I Emulsan Drinking | 56 | 66 | 52 |
| II Emulsan Pretreatment | 70 | 0 | 35 |

TABLE 4

| Group | % Reduction in Caries Compared with Control After | |
|---|---|---|
|  | 5 weeks | 9 weeks |
| I (Emulsan Drinking) | 48 | 63 |
| II (Emulsan Pretreatment) | 42 | 47 |

The results show at 3 weeks, 51% less *S. mutans* in Group I and 61% less in Group II compared with the water control (Table 2). Reductions in total aerobes are 56% and 70% respectively (Table 3). After five weeks, the *S. mutans* count is reduced by 77% (Table 2) and total aerobes by 66% (Table 3) but only in Group I. Group I is found to have 48% less caries than the control and Group II 42% less (Table 4). These results are statistically significant.

At the final sampling after nine weeks, (Tables 2 and 3) reductions of 41% and 52% are obtained for *S. mutans* and total aerobes respectively in Group I and 26% and 35% in Group II. The reduction in caries in Group I is 63% and 47% for Group II (Table 4).

The conclusions from this study are that 1% emulsan in the drinking water is effective in reducing the numbers of both *S. mutans* and other aerobes in hamster plaque. Pretreatment of *S. mutans* with emulsan also reduces their number and consequently total aerobes (subject to the anomolous result after five weeks). There is a consequently large decrease in caries. These results fit the premise that emulsan acts by breaking the bacterial lectin-carbohydrate bond and, possibly, the hydrophobic bonds which allow bacteria to adhere to oral surfaces.

EXAMPLE 3

In vivo tests

Further evaluations are done in tests on hamsters by swabbing hamster teeth twice per day with water control; 0.055% aqueous solution of caries preventing sodium fluoride (250 ppm F$^-$) (Composition W); 0.25% aqueous dispersion of apo-α-emulsan (Composition X); and 1% aqueous dispersion of apo-α-emulsan (Composition Z). The *S. mutans* counts and total aerobes are determined after six and twelve weeks compared to a water control and caries (maxillary and mandible) are determined after 12 weeks; also compared to a water control.

The results are set forth in Tables 5, 6 and 7:

TABLE 5

| Composition | % Difference in *S. Mutans* Compared with Control (Water) | |
|---|---|---|
|  | 6 weeks % | 12 weeks % |
| W (NaF) | 27 reduction | 21 increase |
| X (0.25% emulsan) | 62 reduction | 41 reduction |
| Z (1.0% emulsan) | 63 reduction | 53 reduction |

TABLE 6

| Composition | % Difference in Total Aerobes Compared with Control (Water) | |
|---|---|---|
|  | 6 weeks % | 12 weeks % |
| W (NaF) | 19 reduction | 17 increase |
| X (0.25% emulsan) | 53 reduction | 37 reduction |
| Z (1.0% emulsan) | 40 reduction | 35 reduction |

TABLE 7

| Composition | % Difference in Caries Compared with Control Water After 12 Weeks | |
|---|---|---|
|  | Maxillary % | Mandible % |
| W (NaF) | 74.1 reduction | 90.6 reduction |
| X (0.25% emulsan) | 10.2* reduction | 43.7 reduction |
| Z (1.0% emulsan) | 36.9 reduction | 61.4 reduction |

*(not statistically significant)

The conclusions from this study are that in concentrations of 0.25% and 1%, emulsan is highly effective in removing *S. mutans* and total aerobes and provides a means to effect both a plaque and caries reduction compared to sodium fluoride which is not effective as a plaque reducing agent. The results are statistically significant, except as indicated.

EXAMPLE 4

The following toothpaste is prepared:

|  | PARTS |
|---|---|
| Glycerine | 22.00 |
| Sodium carboxymethyl cellulose | 1.00 |
| Sodium saccharin | 0.20 |
| Sodium benzoate | 0.50 |
| Sodium monofluorophosphate | 0.76 |
| Tetrasodium pyrophosphate | 0.25 |
| Deionized water | 23.44 |
| Apo-α-emulsan | 1.00 |

-continued

|  | PARTS |
| --- | --- |
| Dicalcium phosphate dihydrate | 48.76 |
| Flavor | 0.89 |
| Sodium lauryl sulfate | 1.20 |

EXAMPLE 5

The following mouthwashes are prepared:

|  | A PARTS | B PARTS |
| --- | --- | --- |
| Ethanol | 5.000 | 9.850 |
| Glycerine | 15.000 | 10.000 |
| Sodium fluoride | 0.048 | — |
| Emulsan | 1.000 | 0.500 |
| Polyoxyethylene-polyoxypropylene block copolymer (Pluoronic F108) | — | 1.000 |
| Flavor | 0.003 | 0.150 |
| Benzoic acid | 0.010 | — |
| Sodium benzoate | 0.500 | — |
| Sodium saccharin | 0.020 | 0.040 |
| Color solution | 0.001 | 0.045 |
| Deionized water | 78.418 | 78.415 |

In the foregoing examples, sodium saccharin may be replaced by sodium cyclamate.

Although this invention has been described with reference to specific examples, it will be apparent to one skilled in the art that various modifications may be made thereto which fall within its scope.

We claim:

1. A toothpaste comprising a plaque-inhibiting and caries-reducing amount of emulsan and a dental vehicle containing water in sufficient amount to disperse said plaque-inhibiting amount of emulsan, said vehicle further containing a humectant and gelling agent.

2. The toothpaste claimed in claim 1 wherein said dental vehicle which contains water in sufficient amount to disperse said plaque inhibiting amount of emulsan further contains humectant in amount such that the total liquid content of water and humectant is about 20–75% by weight and about 0.5–10% of said gelling agent.

3. The toothpaste claimed in claim 2 wherein said toothpaste contains about 20–75% of a water-insoluble polishing agent.

4. The toothpaste claimed in claim 3 wherein said emulsan is present in amount of about 0.05–10% by weight of the water in said dental vehicle.

5. The toothpaste claimed in claim 4 wherein said amount of emulsan is about 0.1–3% by weight.

6. The toothpaste claimed in claim 5 wherein said amount of emulsan is about 0.25–1%.

7. The toothpaste claimed in claim 2 wherein said emulsan is apo-α-emulsan.

8. A mouthwash comprising a plaque-inhibiting and caries-reducing amount of emulsan and a dental vehicle containing water in sufficient amount to disperse said plaque-inhibiting amount of emulsan, said vehicle further containing isopropanal or ethanol.

9. The mouthwash claimed in claim 8 wherein said dental vehicle which contains water in sufficient amount to disperse said plaque inhibiting amount of emulsan further contains about 5–25% of isopropanal or ethanol.

10. The mouthwash claimed in claim 9 wherein said emulsan is present in amount of about 0.05–10% by weight of the water in said mouthwash.

11. The mouthwash claimed in claim 10 wherein said amount of emulsan is about 0.1–3% by weight.

12. The mouthwash claimed in claim 11 wherein said amount of emulsan is about 0.25–1% by weight.

13. The mouthwash claimed in claim 9 wherein said emulsan is apo-α-emulsan.

* * * * *